(12) United States Patent
Yamashita et al.

(10) Patent No.: US 7,691,643 B2
(45) Date of Patent: Apr. 6, 2010

(54) MASS ANALYSIS METHOD AND MASS ANALYSIS APPARATUS

(75) Inventors: Hiromichi Yamashita, Hitachinaka (JP); Yoshiaki Kato, Mito (JP)

(73) Assignee: Hitachi High-Technologies Corporation, Tokyo (JP)

( * ) Notice: Subject to any disclaimer, the term of this patent is extended or adjusted under 35 U.S.C. 154(b) by 1109 days.

(21) Appl. No.: 10/561,771

(22) PCT Filed: Jun. 23, 2003

(86) PCT No.: PCT/JP03/07923

§ 371 (c)(1),
(2), (4) Date: Dec. 21, 2005

(87) PCT Pub. No.: WO2004/113905

PCT Pub. Date: Dec. 29, 2004

(65) Prior Publication Data

US 2007/0059842 A1 Mar. 15, 2007

(51) Int. Cl.
*G01N 24/00* (2006.01)
(52) U.S. Cl. .................. 436/173; 436/86; 250/281; 250/282
(58) Field of Classification Search .................. None
See application file for complete search history.

(56) References Cited

U.S. PATENT DOCUMENTS 6,008,490 A 12/1999 Kato

FOREIGN PATENT DOCUMENTS

| JP | 5-164751 | 6/1993 |
|---|---|---|
| JP | 8-124519 | 5/1996 |
| JP | 10-274640 | 10/1998 |
| WO | WO 95/25281 | 9/1995 |

OTHER PUBLICATIONS

Reid, Gavin E, et al. 'Top down' protein characterization via tandem mass spectrometry, 2002, Journal of Mass Spectrometry, vol. 36, pp. 663-675.*

Spahr et al., "Simplification of Complex Peptide Mixtures for Proteomic Analysis: Reversible Biotinylation of Cysteinyl Peptides" Electrophoresis vol. 21, No. 9, pp. 1635-1650, May 2000.

\* cited by examiner

*Primary Examiner*—Yelena G Gakh
*Assistant Examiner*—Robert Xu
(74) *Attorney, Agent, or Firm*—Dickstein Shapiro LLP

(57) ABSTRACT

The invention provides a mass analysis method and apparatus capable of identifying proteins or peptides at greater speed and with improved accuracy. Specifically, a mass analysis method whereby a sample is ionized and a protein is analyzed using a mass analysis apparatus is provided, said method comprising: selecting predetermined information from a database in which information about proteins and peptides is stored, estimating the mass of the selected component, and calculating frequency information for each mass; analyzing a sample using a mass analysis apparatus so as to acquire a mass spectrum, selecting, based on the acquired mass spectrum and said frequency information, a mass to be used for identification, performing mass analysis using the mass spectrum of the selected mass as a precursor ion, and performing an identification process using a resultant mass spectrum. The method allows a precursor ion for obtaining an MS/MS spectrum required for identification processing to be efficiently selected using the frequency information matched with the purpose of analysis.

11 Claims, 9 Drawing Sheets

FIG. 2
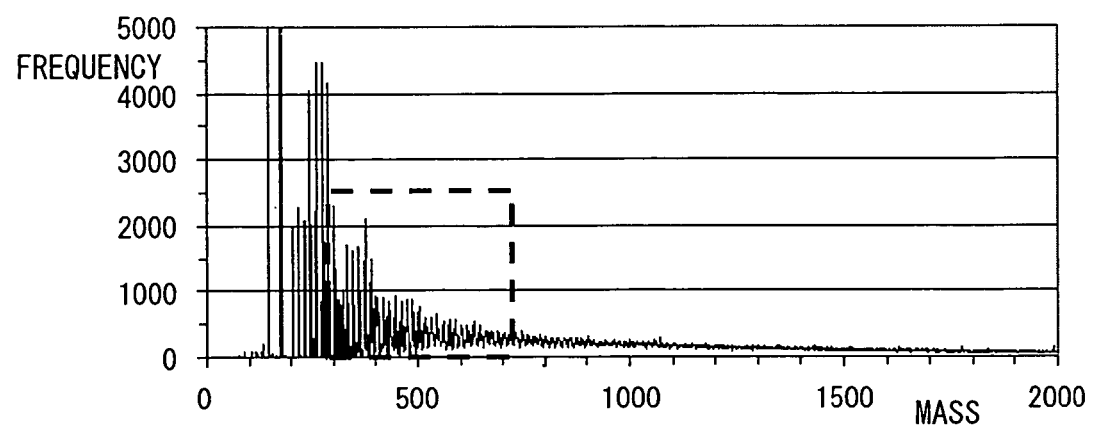
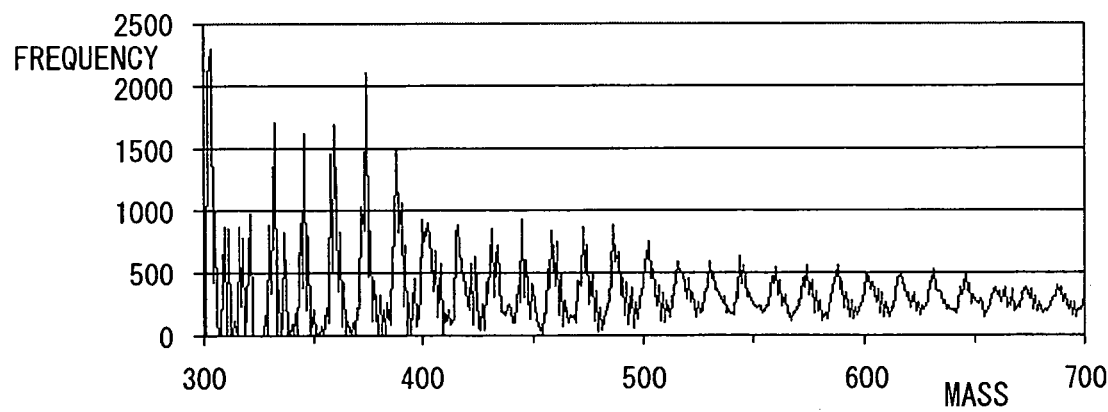

FIG. 4

(a) PROTEIN SELECTION CONDITIONS
DATABASE            SPECIES
[Swiss-prot ▼]      [homo sapiens ▼]
KEYWORD
[zinc finger]

(b) FREQUENCY AND WEIGHT PATTERN CALCULATION CONDITIONS
MODIFICATION       ☐ PHOSPHORIZATION ☐ ACETYLATION ☐ METHYLATION
DIGESTIVE ENZYME   [Trypsin ▼]
METHOD OF IONIZATION [ESI ▼]
MASS ACCURACY (Da) [1]
MASS RANGE (Da)    [50] — [40000]
MASS TYPE          ⦿ MONOISOTOPIC     ◎ AVERAGE (c) FREQUENCY AND WEIGHT PATTERN CALCUATION RESULTS
⦿ FREQUENCY ◎ WEIGHT PATTERN 1 ◎ WEIGHT PATTERN 2

(d) PRECURSOR ION SELECTION AND MS/MS ANALYSIS CONDITIONS
MASS RANGE (Da)                       [300] — [40000]
THRESHOLD OF ION INTENSITY            [10]    [% ▼]
PSEUDOSPECTRUM INTENSITY (LOW FREQUENCY)  [0.5] — [0.001]
PSEUDOSPECTRUM INTENSITY (HIGH FREQUENCY) [1]   — [0.01]
PRECURSOR ION      ⦿ FROM LOW FREQUENCY    ◎ FROM HIGH FREQUENCY
                   ◎ HIGH → LOW ALTERNATELY ◎ LOW → HIGH ALTERNATELY
MS/MS ANALYSIS REPETITION             [3]     [TIMES ▼]

MASS ANALYSIS METHOD AND MASS ANALYSIS APPARATUS

TECHNICAL FIELD

The present invention relates to an apparatus and method for improving the accuracy of identification of proteins in particular and for reducing processing time, using a mass analysis apparatus.

BACKGROUND ART

Generally known methods for identifying proteins or peptides include the Edman degradation method and mass spectrometry.

An example of identification of proteins using a mass analysis apparatus is disclosed in JP Patent Publication (Kohyo) No. 9-510780 A (1997). In this example, a mass spectrum is predicted from public databases in which amino acid sequence information about proteins and peptides is stored. The predicted mass spectrum is compared with the mass spectrum of a sample that has been actually measured, so as to identify the sample based on the degree of correspondence.

An example of analysis of measurement results using public databases for data processing in a mass analysis apparatus is disclosed in JP Patent Publication (Kokai) No. 5-164751 A (1993).

DISCLOSURE OF THE INVENTION

Conventional methods have the following problems:

(a) Protein Identification Accuracy in an Unknown Sample

The mass of an ion that has been determined by measurement could correspond to many peptides in a database where amino acid sequences of proteins are stored. In such a case, it is difficult to identify a protein based on its peptides due to the large number of proteins that contain such peptides.

(b) Time Required for Identification Processing

Identification of proteins or peptides is implemented as a post-measurement data processing. When a database of information about amino acid sequences of proteins or peptide is used, identification accuracy is directly influenced by a change in the contents of the database. For example, when the measurement data is identical, peptides or proteins that have so far been unknown could be identified through the use of a most up-to-date database. In view of such possibility, it is necessary to implement identification processing each time the database is updated. However, this would mean that, in the current situation in which the contents registered in databases are rapidly increasing and the amount of measurement data is also steadily increasing, the time required for identification processing would increase dramatically. Thus, there is a strong need for a method whereby time required for identification processing can be reduced.

(c) Amount of Sample Required for Identification

There are various types of proteins in the cells of living organisms, some existing in large quantities and some in very small quantities. If the purpose is to identify a protein that exists in very small quantities, a measurable amount must be secured. However, many proteins are not readily available or are expensive, depending on the species or the type of tissue.

When a protein is identified using a mass analysis apparatus, a liquid chromatograph mass spectrometer (LC/MS) or a matrix-assisted laser desorption/ionization mass spectrometry (MALDI-MS) is often used. In the LC/MS, a sample eluted from the LC is sequentially introduced into the MS such that the mass spectrum that is measured varies constantly. In the MALDI-MS, a sample that has been preprocessed is disposed on a microplate or the like and irradiated with laser for ionization. Thus, when the amount of sample is very small, ions will also appear in minute amounts and the time in which they can be detected in the form of a mass spectrum will also be very limited.

When protein identification is implemented using a mass analysis apparatus, the so-called MS/MS spectrum is generally used, which is obtained by cleaving ions that have once been obtained, in order to obtain a more detailed mass spectrum. If the obtained mass spectrum constantly changes, or if it appears only for a very small time, in some cases the MS/MS spectrum cannot be obtained at once for all of the ions. In particular, when there are only minute amounts of the target protein or peptide, it is impossible to obtain a mass spectrum by introducing the sample over and over again. Therefore, there is a need for a method whereby identification processing can be implemented using an MS/MS spectrum even when the amount of sample is very small.

(d) Particular Protein Selectivity

When a protein or a peptide is measured using a mass analysis apparatus, in some cases it is desired that a particular protein be made the focus of identification. For example, a particular protein can be selected in accordance with the functional or structural properties of the protein, intra-cell localization information, expression pattern, or association with particular diseases. It is important to enhance protein selectivity and improve the probability of identifying a particular protein, instead of identifying proteins or peptides in a random manner.

Furthermore, if selectivity to proteins other than a particular protein can be improved, it can be expected that, consequently, the probability of identifying impurities or peptides that have been modified after translation will be improved.

It is an object of the invention to provide a mass analysis method and apparatus capable of identifying a protein or peptide at higher speed and with greater accuracy using a mass analysis apparatus.

In order to achieve the aforementioned object, the invention provides a mass analysis method whereby a sample is ionized and a protein is analyzed using a mass analysis apparatus, said method comprising:

selecting predetermined information from a database in which information about proteins and peptides is stored, estimating the mass of a selected component, and calculating frequency information for each mass;

analyzing a sample using a mass analysis apparatus so as to acquire a mass spectrum, selecting, based on the acquired mass spectrum and the frequency information, a mass to be used for identification, performing mass analysis using the mass spectrum of the selected mass as a precursor ion, and performing an identification process using a resultant mass spectrum.

BRIEF DESCRIPTION OF THE DRAWINGS

FIG. 2 shows graphs indicating frequency information accumulated in the first embodiment.

FIG. 4 shows examples of screens for setting condition.

BEST MODES FOR CARRYING OUT THE INVENTION

Embodiments of the invention will be hereafter described.

First Embodiment

Apparatus Configuration

Figure 3:
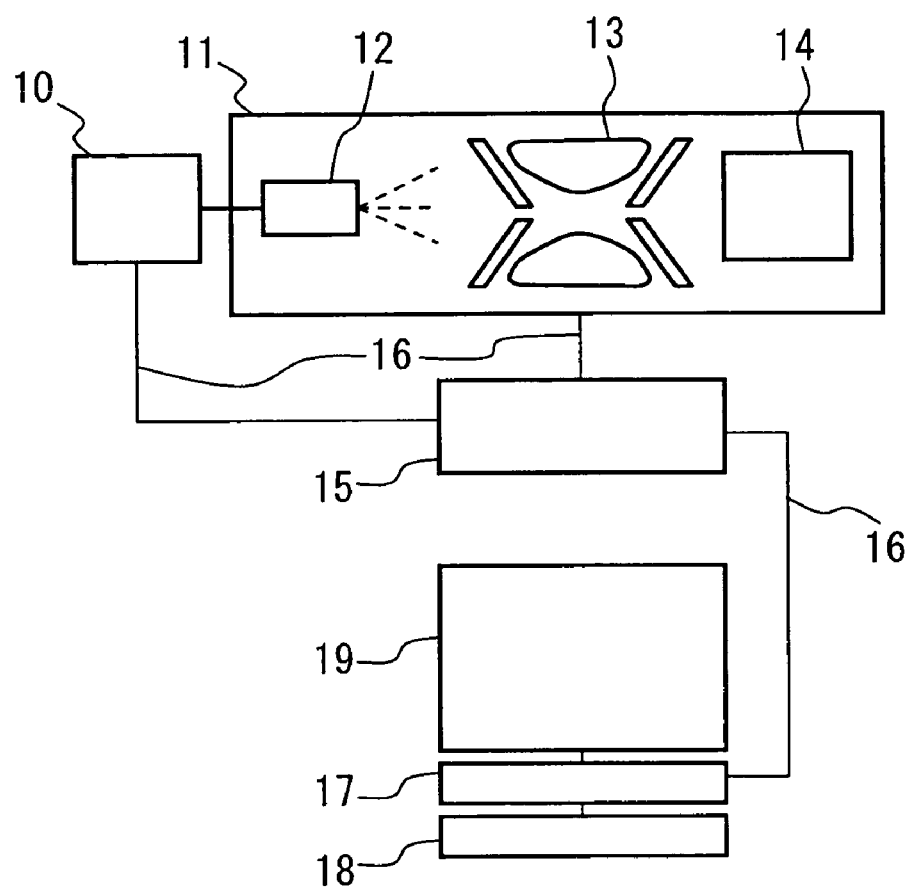
FIG. 3 shows an example of configuration of an apparatus according to the invention.

FIG. 3 shows the configuration of a mass spectrometer and a data processing apparatus to which the invention is applied.

In the present embodiment, a chromatography apparatus 10 for separating a sample, a mass analysis apparatus main body 11, a control unit 15 for the mass analysis apparatus main body, and a data processing unit 17 are connected via signal lines 16. The mass analysis apparatus main body 11 is comprised of an ion source 12 for ionizing a sample, a mass analysis unit 13, and a detection unit 14. The data processing unit 17 includes a keyboard 18 and a display unit 19.

The data processing unit 17 is connectable to external public lines such as the Internet, via which it can access databases connected on networks to obtain necessary information. Information stored in databases may also be obtained through recording media, such as CD-ROMs.

While in the present embodiment a chromatography apparatus and an ion trap type mass spectrometer are illustrated, the mass spectrometer may be comprised of any type of mass spectrometer capable of selecting precursor ion through $MS^1$ analysis and implementing $MS^2$ analysis (so-called "MS/MS analysis"). The ion source is preferably comprised of an ion source capable of ionization with as little destruction of proteins or peptides as possible. One such example is an electrospray ionization source (ESI). The chromatography apparatus is not absolutely necessary, and a mass spectrometer that employs the matrix assisted laser desorption ionization (MALDI) method may also be applied.

Process Contents

Figure 1:
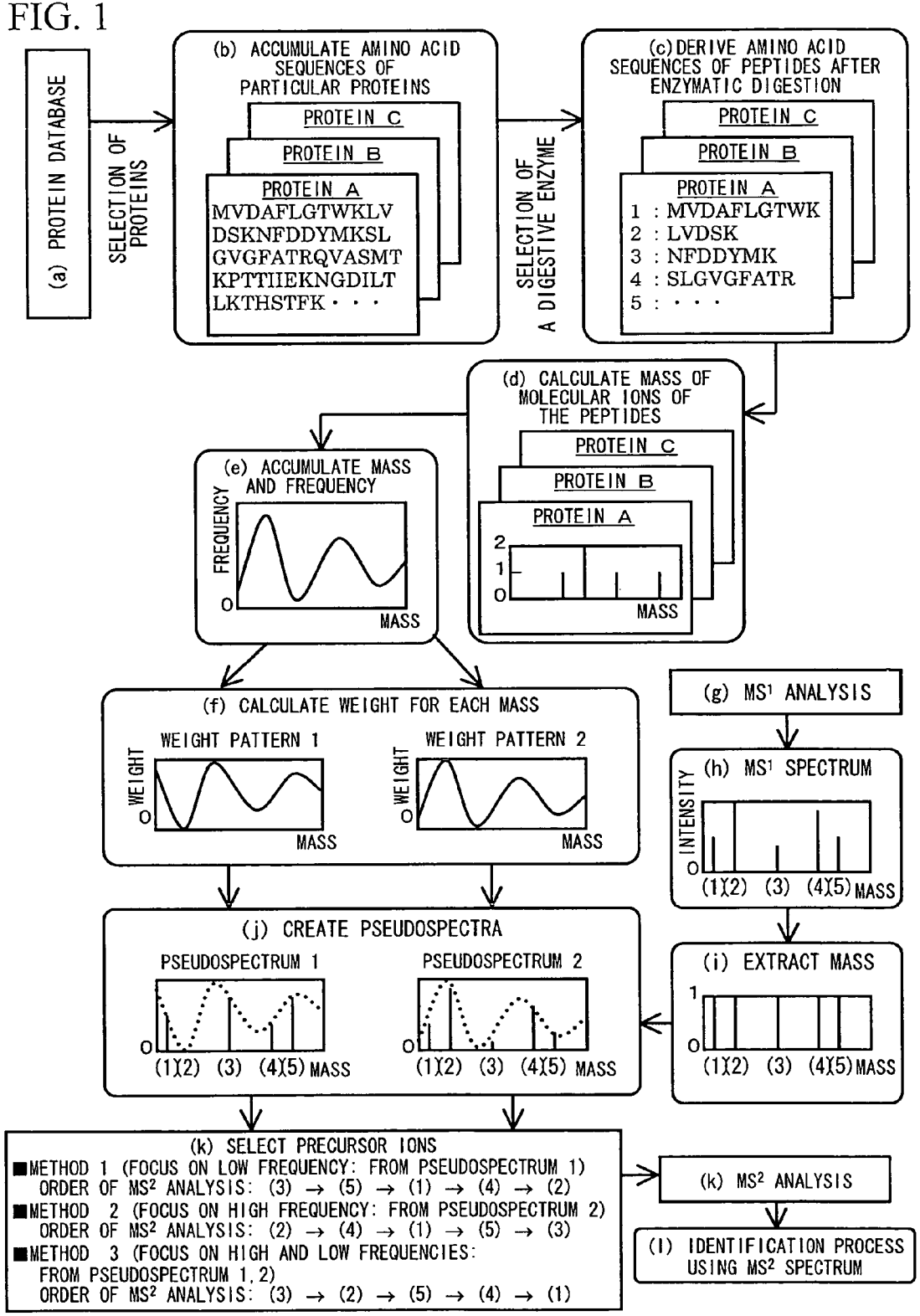
FIG. 1 shows the flow of processes in a first embodiment of the invention.

FIG. 1 shows the basic processes in the present embodiment. For the identification of a protein in the present embodiment, peptides produced by enzymatic digestion of the protein with a predetermined digestive enzyme are subjected to mass analysis, and each peak of the resultant mass spectrum is further cleaved and then subjected to mass analysis (MS/MS analysis), thereby obtaining a mass spectrum that is used for identification. In FIG. 1, a method of selecting precursor ions for MS/MS analysis is shown.

In the present embodiment, a human-derived protein that has been enzymatically digested is assumed as a sample.

In the following, the embodiment is described with reference to FIG. 1.

(a) Database of Proteins

A database of amino acid sequences is selected as a protein database for comparison purposes. When it is a human-derived protein that is under investigation, it is necessary to select a database that contains at least information about species.

One such example is nr (non-redundant protein database) that is published by the NCBI (National Center for Biotechnology Information) of the U.S. This is a collection of amino acid sequences of proteins gathered from various protein databases.

(b) Accumulation of Amino Acid Sequences of Particular Proteins

Amino acid sequences of proteins that are compatible with the purpose of measurement are accumulated from the database (a).

For example, from the amino acid sequences registered in the nr of NCBI, those derived from the databases of proteins (Swiss-Prot) that have been created by the SIB (Swiss Institute of Bioinformatics) and the EBI (The European Bioinformatics Institute) are extracted. From these, amino acid sequences are further accumulated by limiting the species to the human species.

(c) Derivation of Amino Acid Sequences of Peptides after Enzymatic Digestion

The proteins accumulated in (b) are subjected to enzymatic digestion with a predetermined digestive enzyme to produce peptides, and the amino acid sequences of those peptides are determined. The determined sequences are arranged by proteins. The type of digestive enzyme used is designated in advance.

(d) Calculation of the Mass of the Molecular Ions of Peptides

The mass of the peptides of each of the proteins that have been determined in (c) is calculated as it is observed in the form of molecular ions in a mass spectrometer.

The value of mass is rounded off to the whole number. When there is one peptide for each mass, 1 is given, while 0 is given when there is no peptide. When there are a plurality of peptides having the same mass, the number of corresponding peptides is given as the value along the vertical axis for the mass.

(e) Mass and Frequency Accumulation

Data regarding each protein determined in (d) is accumulated for each mass in terms of the relationship between mass and frequency. In the following description, nominal mass will be designated by m and frequency by F, with the value of F corresponding to m expressed by $F_m$.

FIG. 2 shows the frequency for each mass that has been determined on the assumption that human-derived sequences from Swiss-Prot are derived from the nr acquired in December 2002, followed by digestion with trypsin. As will be seen from the figure, large variations are observed in the value of frequency for each mass. This indicates that the number of corresponding peptides varies greatly depending on mass.

(f) Calculation of Weight by Mass

A frequency weight pattern is calculated for each mass determined in (e). The following two patterns are assumed in the present embodiment.

When the weight for each nominal mass (m) is $W_m$, its value can be determined as follows:

$$W_m = 1/(F_m+1) \tag{1}$$

In this equation (1), the weight increases as the frequency becomes closer to zero. The result of this calculation is designated as weight pattern 1.

Thereafter, weight pattern 2 is determined according to the following equation:

$$W_m = 1 - 1/(F_m+1) \tag{2}$$

In this case, the weight increases as the value of the frequency increases, as opposed to the case of weight pattern 1.

Thus, in the present embodiment, two kinds of weight pattern are created, of which one emphasizes lower frequencies while the other emphasizes higher frequencies.

The foregoing processes are prepared prior to making measurement with a mass spectrometer. The processes following (g) below are carried out for an actual sample.

(g) $MS^1$ Analysis

A human-derived sample is subjected to enzymatic digestion according to the same conditions as those in (c) to carry out $MS^1$ analysis.

(h) $MS^1$ Spectrum

The $MS^1$ spectrum obtained through $MS^1$ analysis can be generally determined in terms of a relationship between the mass-to-charge ratio and intensity. The ions that are observed here become the candidates for precursor ions.

(i) Extraction of Mass

From the $MS^1$ spectrum obtained in (h), information about mass is extracted. Specifically, if there is a peak in the $MS^1$ spectrum for each mass that exceeds a predetermined threshold, 1 is given, while 0 is given if there is no such peak. Namely, the presence or absence of peaks corresponding to the mass of interest is indicated by the two values of 0 and 1. It is noted that the mass is rounded to the whole number so as to maintain consistency with the weight patterns. When the binarized value is E, the value of E for each nominal mass (m) can be represented as $E_m$.

(j) Creation of Pseudospectra

Based on the presence or absence of peaks determined in (i) and the weight patterns determined in (f), pseudospectra are created. When the weight pattern is $W_m$ and the presence or absence of a peak is $E_m$, the intensity $I_m$ of a pseudospectrum can be determined by the following equation:

$$I_m = W_m \times E_m \quad (3)$$

In this equation, the intensity of a pseudo-peak reflects the value of the weight pattern. When two kinds of weight pattern are adopted, the pseudospectrum is also created in two kinds. Namely, weight pattern 1 is reflected in a pseudospectrum 1 and weight pattern 2 is reflected in a pseudospectrum 2.

(k) Selection of Precursor Ions and MS/MS Analysis

Precursor ions for which $MS^2$ analysis is to be carried out are selected by focusing on the intensity of the pseudospectra determined in (j). In the following, an example of how precursor ions are selected using pseudospectra 1 and/or 2 will be described with reference to methods 1, 2, and 3.

In method 1, precursor ions are selected using pseudospectrum 1. Specifically, precursor ions are selected in order of decreasing value of the intensity of pseudospectrum 1. Here, weight pattern 1, in which masses of lower frequencies are emphasized, is adopted in pseudospectrum 1. Namely, the masses of the precursor ions selected here appear at lower frequencies in the amino acid sequences of peptides after enzymatic digestion that have been determined in (c).

In the example shown in FIG. 1, the masses of precursor ions are determined in order of (3)→(5)→(1)→(4)→(2), followed by the implementation of MS/MS analysis.

In method 1, when the frequency is zero, the intensity of the pseudospectrum becomes 1. This means that there is no information about corresponding peptides in the database. When protein identification processing is assumed after measurement, it is desirable that there is at least one corresponding peptide. Therefore, the masses for which the intensity becomes 1 should be eliminated. When the frequency is high, the intensity of the pseudospectrum exhibits values close to zero. In such a case, it would not make much sense to focus on the masses of lower frequencies. Thus, in the selection of precursor ions, the range of intensity is important. Therefore, it is important to designate the range of intensity of pseudospectra in advance and then select precursor ions within such a range in order of decreasing intensity.

If a mass such that the intensity of pseudospectrum becomes 1 (frequency is 0) is selected as a precursor ion, the precursor ion could possibly correspond to a peptide that is derived from an unknown protein that does not fall within the calculation conditions according to which the mass has been determined in (d). Even if the protein fall within the calculation conditions, the mass could possibly have been increased or decreased due to post-translation modification. Conversely, if such peptides are desired to be obtained preferentially, precursor ion candidates are limited to masses such that the intensity of pseudospectrum is 1.

When precursor ions are selected in order of decreasing intensity of pseudospectrum after eliminating the masses such that the intensity of the pseudospectrum becomes 1 (frequency is 0), this indicates that there is information about corresponding peptides in the database and that the number of such peptides is relatively small. This means that, when the peptides or proteins are identified in postprocessing after measurement, the peptides or proteins can be narrowed from a smaller number of candidates. As a result, the accuracy of identification of peptide or protein can be improved. This can directly contribute to the reduction of the amount of sample when measurement is repeated until target components have been identified. Furthermore, when the number of candidate peptides is small, the time required for narrowing can also be reduced.

In method 2, precursor ions are selected from pseudospectrum 2, in which the masses of higher frequencies are emphasized. In this case, too, precursor ions are selected in order of decreasing intensity. When precursor ions are selected by this method, the masses of the precursor ions appear with high frequency in the amino acid sequences of peptides after enzymatic digestion that have been determined in (c). Thus, method 2 is suitable when a large number of corresponding proteins are to be selected during the identification of proteins after measurement.

In the example shown in FIG. 1, the precursor ions are selected in order of (2)→(4)→(1)→(5)→(3), and then MS/MS analysis is carried out.

In the case of method 2, there is an increased possibility of obtaining information about a group of proteins having the same sequence information, including proteins derived from orthologous genes that have common ancestry among different species, proteins derived from paralogous genes in which mutation has accumulated after gene duplication within the species, and proteins derived from splice variants in which different mRNA is generated from the same gene regions on the genome.

In method 3, the precursor ions that have been ordered by methods 1 and 2 are alternately adopted. In the example shown in FIG. 1, the result of selection by method 1 is given priority, such that the order (3)→(2)→(5)→(4)→(1) is adopted. In this case, by designating the masses of low frequency and high frequency in sequence, protein identification accuracy during the identification of proteins after measurement can be improved and, therefore, the method is suitable when a wide variety of proteins is to be selected.

Which one of methods 1 to 3 is to be adopted, and whether the high frequency or low frequency is to be given priority in method 3, are designated prior to measurement. In the foregoing description, the influence of isotopes and multivalent ions is omitted.

In the present embodiment, there is provided the functionality whereby, instead of associating all of the peaks in the mass spectrum obtained by mass analysis of an actual sample with precursor ions, how far down the list of the masses the selection of precursor ions should go can be set in advance. When an analysis is carried out with LC/MS, or when minute amounts of a sample are analyzed using MALDI-MS, for example, the time in which the candidate peaks for precursor ions such as (1) to (5) are observed is limited. Therefore, it is often the case that not enough time is available for MS/MS analysis for all of the peaks in the mass spectrum. In such a case, it is very effective to select precursor ions by ordering the masses in order of decreasing validity, as in the present embodiment.

Namely, in the case of MALDI-MS or the like, considering the time in which peaks of precursor ion candidates are expected to be observed, the number of precursor ions that are selected is maximized within the range in which measurement can be made in that time. In the case of LC/MS or the like, because it is necessary to complete analysis within the time in which precursor ion candidates are observed, the number of precursor ions is set in consideration of the time required for MS analysis and MS/MS analysis.

(1) Identification Process Using MS/MS Spectrum

Finally, an identification process is carried out using the MS/MS spectrum of the precursor ions selected in the above step (k). In the identification process, the data collected in the above step (c) and the MS/MS spectrum obtained as a result of analysis of the precursor ions are used.

Thus a series of processes is completed.

In the following, the correspondence between the apparatus configuration shown in FIG. 3 and the contents of the processes shown in FIG. 1 is described. The processes starting from the accumulation of amino acid sequences of particular proteins to the calculation of weights for each mass shown in FIG. 1 are implemented in the data processing unit 17. Weight patterns 1 and 2 created in this unit are transferred to the control unit 15 prior to the start of analysis of the sample. During measurement, the sample is subjected to $MS^1$ analysis in the control unit 15, whereby an $MS^1$ spectrum is acquired. Then, individual processes for the extraction of mass, creation of a pseudospectrum, and selection of precursor ions are performed. In the control unit 15, $MS^2$ analysis is performed on the selected precursor ions, thereby acquiring an $MS^2$ spectrum. In some cases, the process for acquiring an $MS^2$ spectrum from the precursor ions is repeated. Such is the basic flow of the processes as the method shown in FIG. 1 is applied to the apparatus configuration shown in FIG. 3.

Thus, the present embodiment is based on the assumption that $MS^1$ analysis and $MS^2$ analysis are performed each time a sample is introduced. If the same sample can be introduced over a plurality of times, it becomes also possible to select precursor ions by the method of the invention in a single batch after all of the $MS^1$ spectra have been obtained in the first measurement, and then the second and subsequent measurements can be performed. In this case, the selection of precursor ions is carried out not by the control unit 15 but by the data processing unit 17.

During measurement, the designation of precursor ions can be changed depending on the time that has elapsed from the start of measurement, for example.

Screen for Setting Measurement Conditions

FIG. 4 shows screens for the setting of various conditions, which is carried out before measuring a sample. The settings of the conditions are assumed to be realized using the display unit 19 and the keyboard 18 in the data processing unit 17 shown in FIG. 3.

Via the screens shown in FIG. 4, it is possible to set protein selecting conditions, frequency and weight pattern calculation conditions and results, and conditions for the selection of precursor ions and MS/MS analysis, for example. In the following, these conditions are described briefly.

(a) Protein Selection Conditions

In this portion, a database and the species are selected from lists as conditions for the accumulation of amino acid sequences of particular proteins from a protein database. A keyword corresponding to a desired function or the like is also set. In the illustrated example, "Swiss-Prot" is selected as the database and "homo sapiens" (human) is selected as the species. In the keyword blank, "zinc finger" is entered, which refers to a functional site that is found in proteins that bind to DNA. Proteins with such a functional site are considered to be possibly involved with transcription from DNA to mRNA. Namely, the designation calls for the accumulation of human-derived proteins in Swiss-Prot that are related to zinc finger.

(b) Frequency and Weight Pattern Calculation Conditions

In this portion, after the amino acid sequence of the particular proteins designated in (a) are accumulated, conditions for the calculation of frequency information corresponding to mass are set. First, corresponding type of modification and a digestive enzyme are selected. Then, an ionization method, which has an influence on the mass of a molecular ion, is selected. Furthermore, mass accuracy for the calculation of frequency, the range of calculation, and the definition of mass are designated.

While the details of the setting of modification are omitted, it is important also to designate the modification site and the probability of modification, for example. With regard to the designation of digestive enzyme, although it is conceivable to provide additional designation for a possible case of insufficient digestion, such designation is omitted herein.

(c) Frequency and Weight Pattern Calculation Results

In this portion, designated calculation results regarding frequency, weight pattern 1, and weight pattern 2 are displayed in a graph. The graph is preferably adapted for enlargement or reduction in size as required.

(d) Selection of Precursor Ions and MS/MS Analysis Conditions

In this portion, various conditions for the selection of precursor ions are set.

First, the range of mass for limiting the masses of precursor ions is entered, and the threshold value of ion intensity in the $MS^1$ mass spectrum is set. Thereafter, the range of intensity for the selection of precursor ions from pseudospectra is designated for cases of low frequency and high frequency. Further, a condition for the selection of precursor ions is selected from "From low frequency", "From high frequency", "High→low alternately" and "Low→high alternately". It is also possible to designate the value and unit of conditions for the repetition of MS/MS analysis so that the number of precursor ions to be selected can be designated in terms of the number of times and the duration of time, for example. The unit can be designated from a pull-down menu. When the number of times is designated, the value indicates the number of times an MS/MS analysis is carried out. Namely, this is a designation regarding how far down the prioritized-list of the ions, which are ordered by the method designated in the "Precursor ion" section, one should go in designating precursor ions. When the time is designated, the value indicates the time that will elapse from the selection of precursor ions by MS analysis till the end of the last MS/MS analysis. If the time that is set here is exceeded, no MS/MS analysis is carried out on the next candidate ion.

Display of Measurement Results

Figure 5:
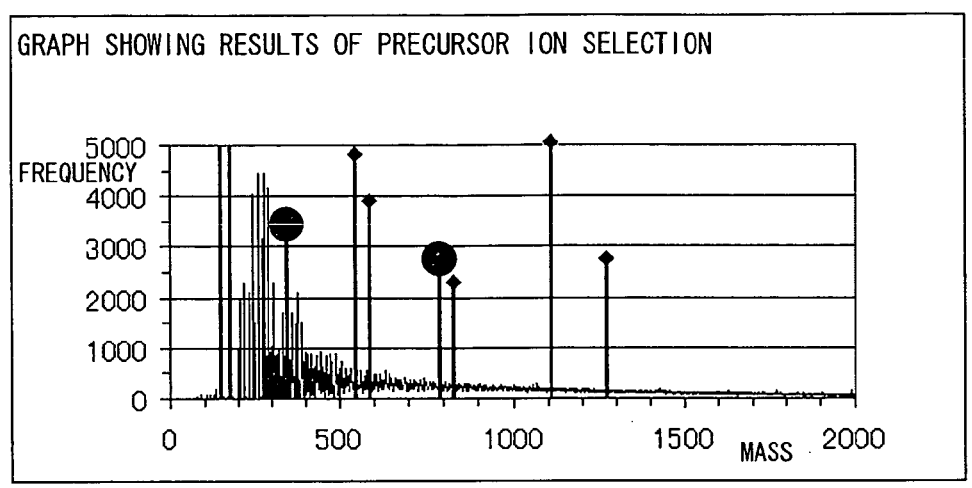
FIG. 5 shows examples of screens displaying the result of selection of precursor ions.

FIG. 5 shows a graph and a table of the results of selection of precursor ions.

In the graph, frequency information that is obtained from the information extracted from a database in advance is displayed overlapping a mass spectrum obtained by actually analyzing a sample. Ions that are selected as precursor ions are indicated by dots shown at the top of peaks, while ions that are not selected are indicated by diamonds. This graph is also preferably adapted for enlargement or reduction in size.

The displayed table shows the mass, ion intensity, and frequency of each mass spectrum, and whether or not a particular ion is selected. In the illustrated example, the ions are sorted in order of increasing frequency in line with the setting of "From low frequency" for the selection of precursor ions in FIG. 4. Thus, the table allows the user to focus on frequency.

In accordance with this display screen, the precursor ions and precursor ion candidates that have been selected from the mass spectrum, and the frequency information that has been applied, are simultaneously displayed in the display unit 19 after measurement, via the data processing unit 17. Therefore, it is possible to verify whether or not precursor ions have been selected according to the designated conditions.

Second Embodiment

In this embodiment, amino acid sequences of proteins that have been accumulated in advance are arranged in terms of mass and frequency of each protein.

Figure 6:
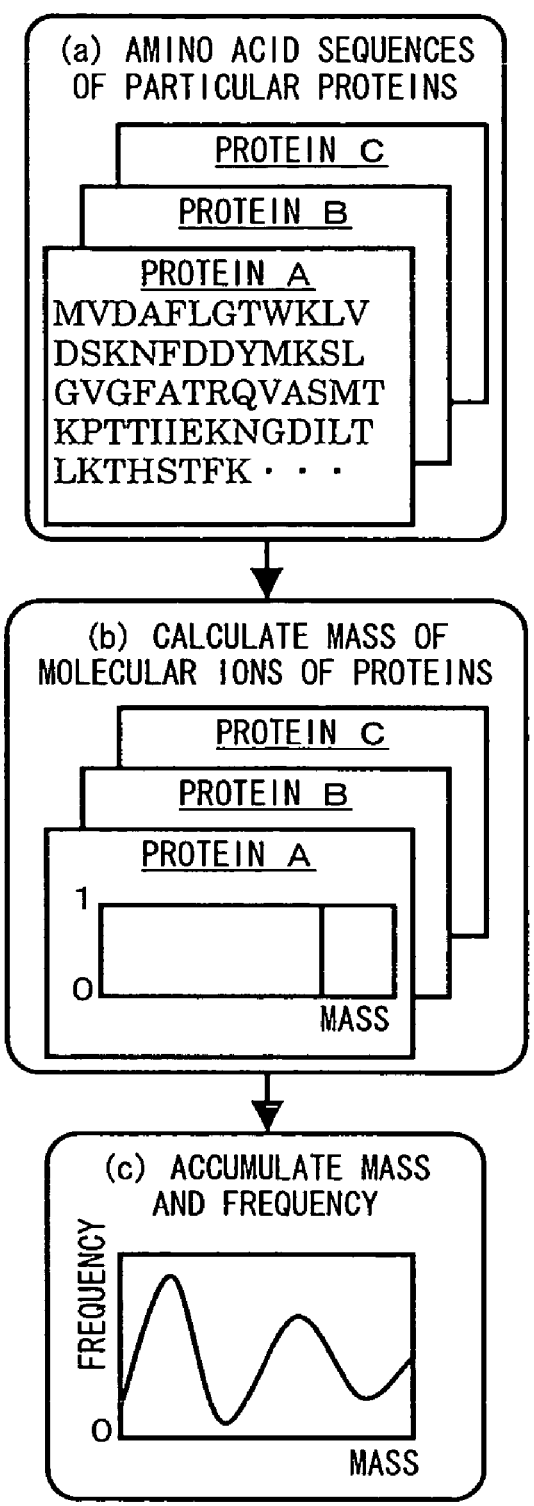
FIG. 6 shows the flow of processes in a second embodiment of the invention.

In this embodiment, too, the flow of the procedure is similar to that shown in FIG. 1. The difference lies in the process whereby the amino acid sequences of particular proteins that have been accumulated are accumulated in terms of mass and frequency (namely, the amino acid sequences of peptides after enzymatic digestion are not calculated, in contrast to the process shown in FIG. 1). FIG. 6 shows a relevant portion of the process.

The basic flow of the process is described with reference to FIG. 6.

(a) Amino Acid Sequences of Particular Proteins

As in the amino acid sequences of particular proteins shown in FIG. 1, amino acid sequences corresponding to target proteins are accumulated from a protein database based on the designation of the species or the like.

(b) Calculation of the Mass of Molecular Ions of Proteins

The mass of each protein accumulated in (a) is calculated as it is observed as a molecular ion. The value of the mass is rounded off to the whole number. When a molecular ion corresponding to a mass exists, 1 is given, while 0 is given when there is no such molecular ion.

(c) Mass and Frequency Accumulation

The data about individual proteins obtained in (b) is accumulated and accumulated in terms of mass.

Figure 7:
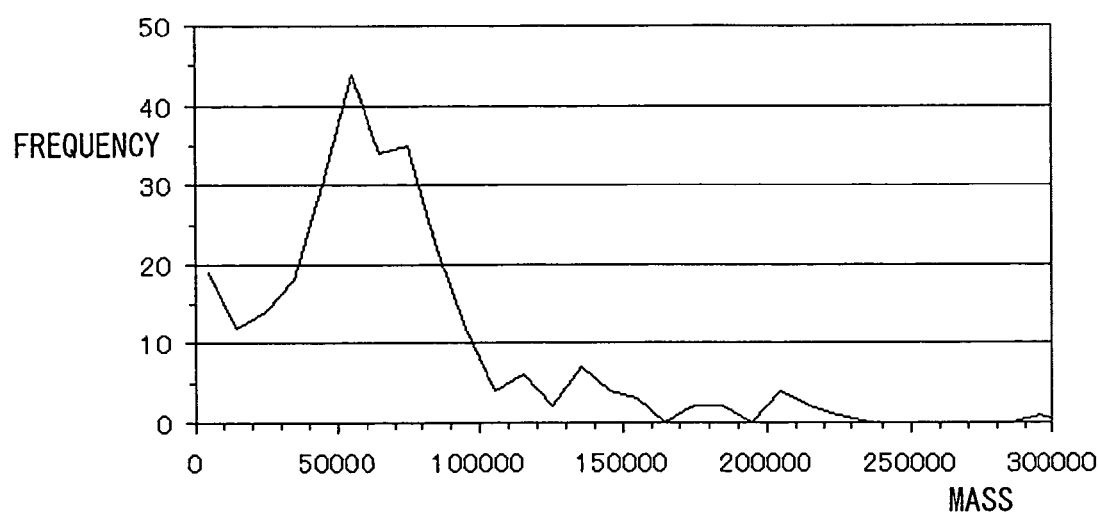
FIG. 7 shows a graph indicating frequency information accumulated in the second embodiment.

FIG. 7 shows a result of accumulating human-derived proteins in Swiss-Prot that denote "zinc finger" and then arranged as frequency information. Namely, the figure indicates the distribution of molecular weights of the thus accumulated proteins.

Since many proteins have very large molecular weights, it is difficult to measure such proteins using a conventional quadrupole mass spectrometer or ion-trapping mass spectrometer. When these apparatuses are used, identification is performed on the basis of peptides obtained by enzymatic digestion, as in the first embodiment. In contrast, the present embodiment assumes the use of a mass analysis apparatus (such as a time-of-flight mass spectrometer, or TOF-MS) capable of measuring proteins by themselves. By applying frequency information to such an apparatus in the present embodiment, it becomes possible to selectively analyze proteins having particular masses without enzymatically digesting them into peptides.

Third Embodiment

The present embodiment shows an example in which selectivity to particular proteins is improved. In particular, attention is focused on proteins having a functional site referred to as "zinc finger," which is believed to be involved with gene expression. This embodiment is an extension of the embodiment shown in FIG. 1.

Figure 8:
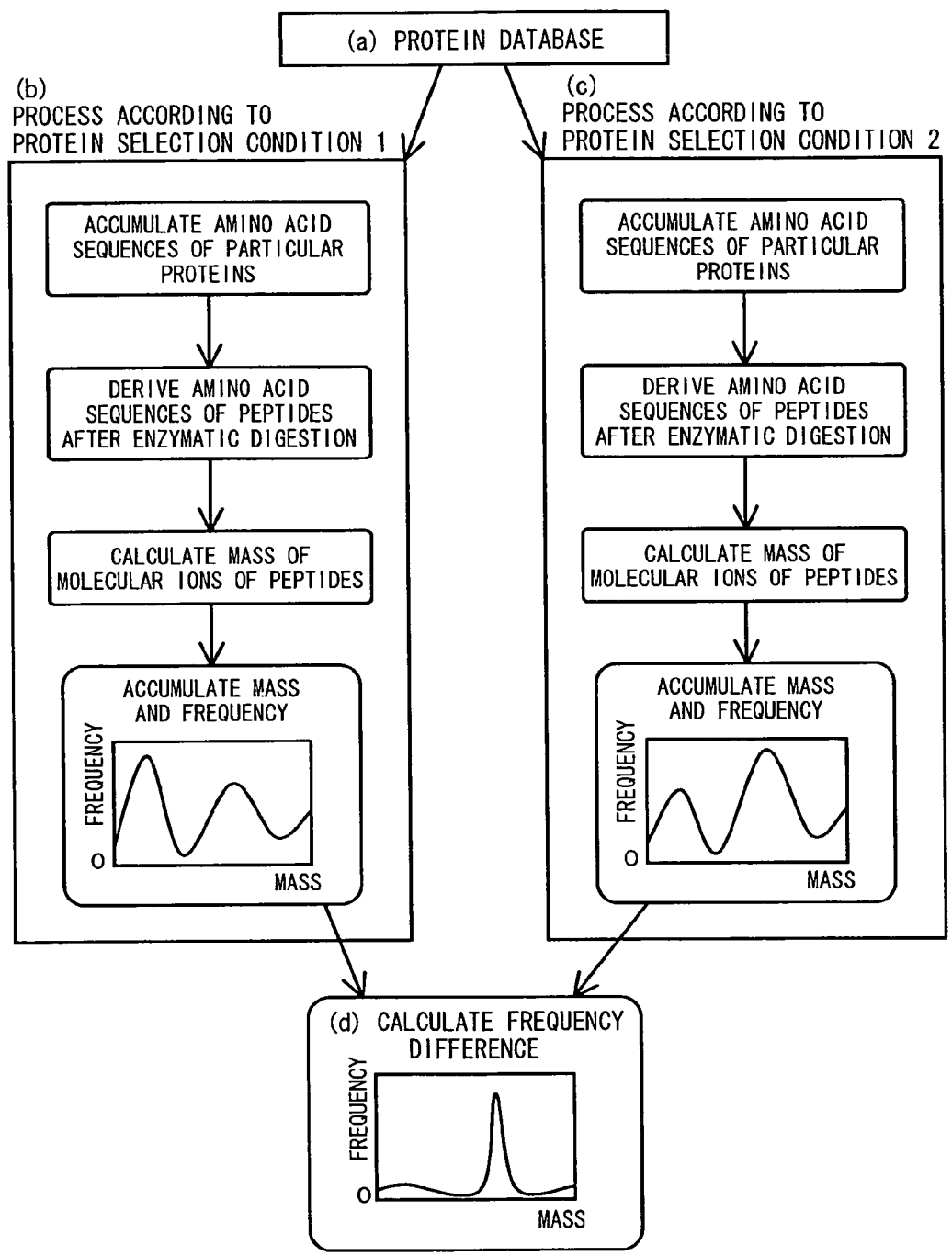
FIG. 8 shows the flow of processes in a third embodiment of the invention.
Figure 9:
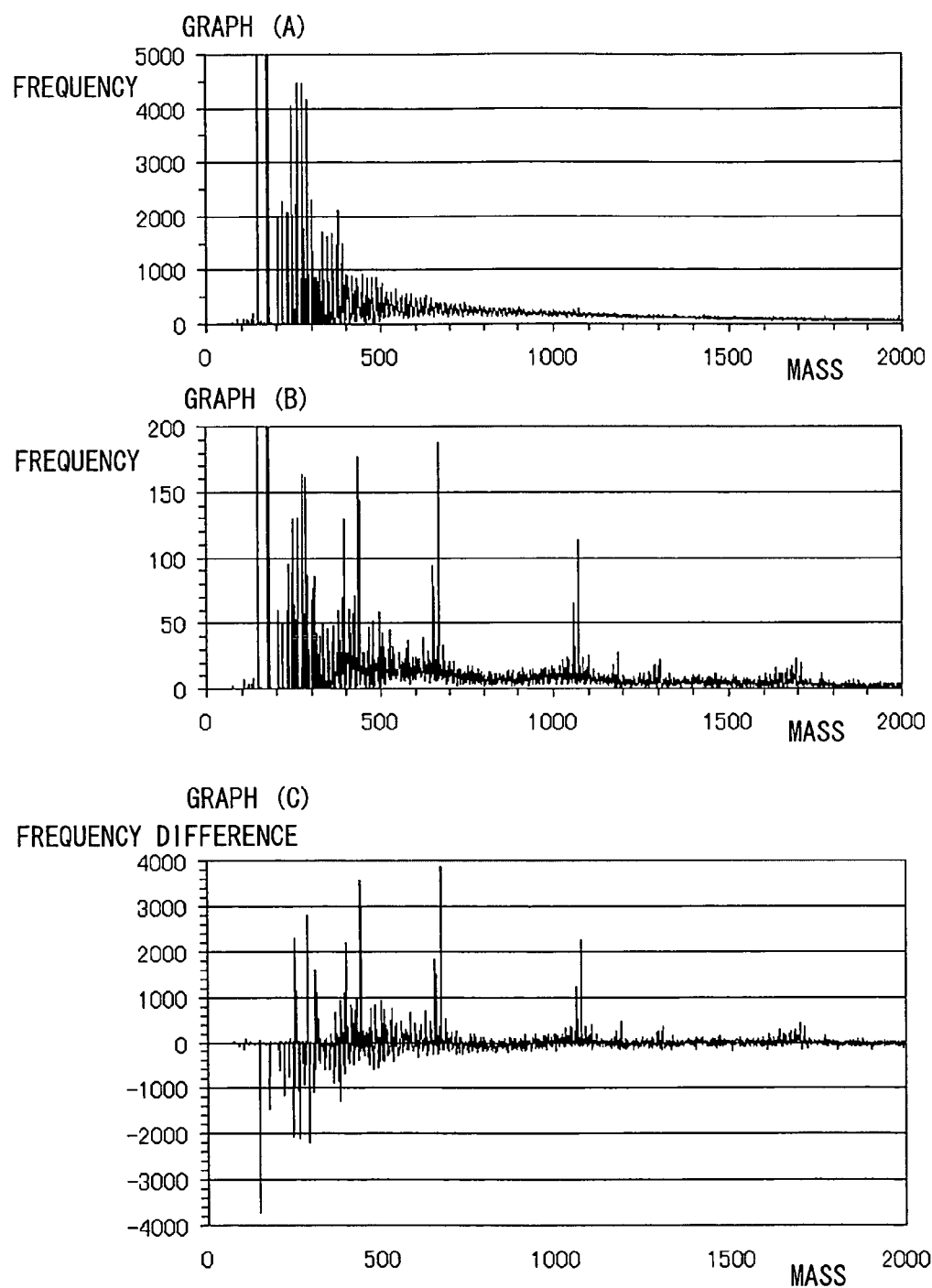
FIG. 9 shows graphs indicating frequency information accumulated in the second embodiment.

FIG. 8 shows the outline of the embodiment. In this example, the flow of FIG. 1 up to the accumulation of mass and frequency is multiplexed, and a frequency difference is determined from the individual results. FIG. 9 shows graphs as examples of the calculation of frequency.

In the following, the outline of the embodiment is described with reference to the flow shown in FIG. 8.

(a) Database of proteins

As in the amino acid sequences of particular proteins shown in FIG. 1, amino acid sequences corresponding to target proteins are accumulated from a protein database based on the designation of the species or the like.

(b) Process According to Protein Selection Condition 1

From the protein database of (a), particular proteins are selected according to selection condition 1. This is followed by the accumulation of amino acid sequences, derivation of amino acid sequences of peptides after enzymatic digestion, calculation of the mass of molecular ions of peptides, and accumulation of the mass and frequency. This flow is the same as that of the processes shown in FIG. 1.

The graph (A) in FIG. 9 shows an example of the result of processing according to protein selection condition 1. The graph shows the frequency in a case where human-derived proteins have been accumulated from Swiss-Prot and digested with trypsin.

(c) Process According to Protein Selection Condition 2

Particular proteins are selected from the protein database of (a) according to selection condition 2. This is followed by the accumulation of amino acid sequences, derivation of amino acid sequences of peptides after enzymatic digestion, calculation of the mass of molecular ions of the peptides, and accumulation of the mass and frequency. This flow is the same as that of the processes shown in FIG. 1.

This process differs from the process according to protein selection condition 1 in (b) in the condition for the selection of proteins. The graph (B) of FIG. 9 shows an example of the result of processing according to protein selection condition 2. This example is based on a case where human-derived proteins are accumulated from Swiss-Prot that denote "zinc finger" and digested with trypsin.

(d) Calculation of Frequency Difference

The relationships between the mass and frequency that have been determined in (b) and (c) are subtracted for each mass so as to find a difference therebetween. If the total number of frequencies is different between them, correction is made by multiplying their ratio, for example.

The graph (C) in FIG. 9 shows an example of the calculation of frequency difference. The example is obtained by subtracting graph (A) from graph (B) for each mass. It is noted, however, that, since the total number of peptides is different between graphs (A) and (B), correction was made by multiplying graph (B) with the ratio of the total number of peptides in one graph to that in the other. In this graph (C), masses such as 667 and 1072 stand out. There is the possibility that these masses are associated with many peptides that are common to zinc finger. The peptide (IHTGEKPYK; single-letter notation of amino acids) associated with 1072 is often found in zinc finger, and it is very important to select this peptide as a precursor ion for the identification of zinc finger.

Namely, by selecting masses with high frequency values as precursor ions based on the frequency information of graph (C), selectivity to proteins related to zinc finger can be improved.

In the illustrated example, the amino acid sequences of proteins registered in the database are utilized as they are. However, some amino acid sequences of proteins are known to be repeated at high frequency. In some cases, it is preferable to ignore such repetition sequences.

In other applications, the protein selection condition may be determined in consideration of the species, protein function, structural properties, localized site within cells, expression pattern, particular diseases, or the source of data, for example. In this way, selectivity to peptides derived from particular proteins could be improved.

In the field of study concerned with signal transmission, for example, phosphorylation of tyrosine is of great significance. Therefore, the method for improving the selectivity to peptide fragments of proteins of concern in which tyrosine has been phosphorylated is believed to be useful. When the frequency information for unmodified proteins is created, mass difference arises due to modification. Thus, by selecting masses with lower frequency, selectivity to modified peptides increases. Furthermore, a method for finding a strict difference in frequency information between nonmodified and modified proteins could also be significant.

It is difficult to purify proteins that exist in trace amounts in living tissues. Particularly when it is necessary to identify a protein or peptide that constitute impurities, it is useful to improve the selectivity to matters other than target substances. In this case, too, selectivity to impurities can be expected to improve by creating frequency information regarding target proteins and then selecting precursor ions while focusing on the masses of lower frequency.

As described above, in accordance with the invention, precursor ions for acquiring a MS/MS spectrum necessary for identification can be efficiently selected using frequency information that is matched with the purpose of analysis. Thus, improved identification accuracy can be achieved and processing time can be reduced.

The invention claimed is:

1. A mass analysis method comprising:
   obtaining amino acid sequences from protein information and stored in a database;
   estimating a mass for each of said amino acid sequences;
   calculating a number of occurrences for each of said masses;
   subsequently, obtaining a mass spectrum by performing an MS analysis of a sample with a mass analysis apparatus;
   selecting a precursor ion based on the obtained mass spectrum and the calculated numbers of occurrences;
   performing an MS/MS analysis of the selected precursor ion; and
   performing an identification process using a mass spectrum obtained through the MS/MS analysis.

2. The mass analysis method according to claim 1, further comprising, when the mass of the component information obtained from said database is estimated, estimating a peptide that will be obtained by enzymatically digesting each protein with a predetermined digestive enzyme, and estimating the mass of each peptide.

3. The mass analysis method according to claim 1, further comprising pre-setting the number of said precursor ions that are selected.

4. A mass analysis method whereby a sample is ionized and a protein is analyzed using a mass analysis apparatus, comprising the steps of:
   (A) obtaining information about a plurality of proteins from an external database in which information about proteins is stored;
   (B) estimating masses of peptides corresponding to said plurality of proteins;
   (C) calculating a weight pattern by conducting normalization such that 1 is given when there is an estimated mass and 0 is given when there is no estimated mass;
   (D) measuring a sample and acquiring a mass spectrum;
   (E) normalizing the spectrum of the sample such that 1 is given for each mass, when there is a mass, and 0 is given when there is no mass;
   (F) creating a pseudospectrum by superposing said spectrum of an actual sample that has been normalized on said weight pattern; and
   (G) selecting a precursor ion to be subjected to MS/MS analysis from said mass spectrum of said sample based on the created pseudo spectrum.

5. The mass analysis method according to claim 4, further comprising creating, when said weight pattern is calculated, a first pattern in which masses of lower frequencies are emphasized for and a second pattern in which masses of higher frequencies are emphasized.

6. The mass analysis method according to claim 5, wherein the mass for which the weighting value indicates the highest value in said second pattern is eliminated when the precursor ion to be subjected to MS/MS analysis is selected.

7. The mass analysis method according to claim 4, wherein a plurality of conditions are set when information is obtained from said database, and said steps (B) and (C) are performed for each item of information obtained in accordance with each of said set conditions, and the difference in frequency of the weight patterns according to each of said set conditions is determined so as to obtain a new weight pattern.

8. A mass analysis apparatus comprising:
   an ionization unit for ionizing a sample;
   a mass analysis unit for performing mass analysis; and
   a data processing unit for setting analysis conditions and performing data processing on an analysis result,
   wherein the data processing unit performs
      a preparation process in which, in accordance with a preset condition, amino acid sequences are obtained from protein information stored in a database, a mass is estimated for each of said amino acid sequences, and a number of occurrences is calculated for each mass, and
      a precursor ion selection process in which, after the preparation process, a precursor ion to be subjected to MS/MS analysis is selected in light of a mass spectrum obtained through a mass analysis of an actual sample and in accordance with the calculated numbers of occurrences.

9. The mass analysis apparatus according to claim 8, wherein said data processing unit comprises a display unit, wherein said display unit displays said number of amino acid sequences for each of the masses, wherein said mass spectrum obtained by mass analysis of said actual sample is superposed on the displayed contents.

10. The mass analysis apparatus according to claim 8, wherein whether or not each of the peaks in said mass spectrum obtained by mass analysis of said actual sample has been selected as a precursor ion is displayed.

11. The mass analysis method according to claim 4, further comprising designating a range of intensity of the pseudospectrum, and selecting the precursor ion within the designated range in order of decreasing intensity.

* * * * *